US010816493B2

(12) United States Patent
Lee et al.

(10) Patent No.: US 10,816,493 B2
(45) Date of Patent: Oct. 27, 2020

(54) ELECTRICAL MEASUREMENT METHOD, ELECTRICAL MEASUREMENT DEVICE, AND BLOOD CONDITION ANALYSIS SYSTEM

(71) Applicant: SONY CORPORATION, Tokyo (JP)

(72) Inventors: Seungmin Lee, Kanagawa (JP); Kenzo Machida, Kanagawa (JP); Kaori Kawaguchi, Saitama (JP); Marcaurele Brun, Tokyo (JP)

(73) Assignee: SONY CORPORATION, Tokyo (JP)

( * ) Notice: Subject to any disclaimer, the term of this patent is extended or adjusted under 35 U.S.C. 154(b) by 108 days.

(21) Appl. No.: 15/560,039

(22) PCT Filed: Feb. 29, 2016

(86) PCT No.: PCT/JP2016/056020
§ 371 (c)(1),
(2) Date: Sep. 20, 2017

(87) PCT Pub. No.: WO2016/158148
PCT Pub. Date: Oct. 6, 2016

(65) Prior Publication Data
US 2018/0073997 A1 Mar. 15, 2018

(30) Foreign Application Priority Data
Mar. 31, 2015 (JP) .................. 2015-072656

(51) Int. Cl.
G01N 27/02 (2006.01)
G01N 33/49 (2006.01)
(Continued)

(52) U.S. Cl.
CPC ......... G01N 27/02 (2013.01); G01N 33/4905 (2013.01); G01N 33/86 (2013.01); G01N 33/491 (2013.01); G01N 33/80 (2013.01)

(58) Field of Classification Search
CPC .... G01N 27/02; G01N 33/86; G01N 33/4905; G01N 33/80; G01N 33/491
See application file for complete search history.

(56) References Cited

U.S. PATENT DOCUMENTS

2009/0311675 A1 12/2009 Hosokawa
2012/0149035 A1* 6/2012 Burd .................... B01J 19/0046
135/7.21

(Continued)

FOREIGN PATENT DOCUMENTS

CN 101292161 A 10/2008
CN 104919309 A 9/2015
(Continued)

OTHER PUBLICATIONS

Baskurt, Oguz et al. Red Blood Cell Aggregation. CRC Press, 2011, Boca Raton, FL. (Year: 2011).*

(Continued)

Primary Examiner — Christopher Adam Hixson
(74) Attorney, Agent, or Firm — Chip Law Group

(57) ABSTRACT

Provided is a technique that allows high-accuracy electrical measurement without the influence of blood sedimentation in a case where various measurements or evaluations are performed using blood samples containing a blood cell component and a plasma component. Provided is an electrical measurement method for electrically measuring a blood sample including at least a blood cell component and a plasma component, the electrical measurement method including the step of adding a blood sedimentation inhibitor to the blood sample. Also provided is a blood sedimentation inhibitor for use in electrical measurement of a blood sample including at least a blood cell component and a plasma component, the blood sedimentation inhibitor including a non-cationic water-soluble compound and being capable of (Continued)

increasing specific gravity and/or viscosity of the plasma component.

9 Claims, 4 Drawing Sheets

(51) Int. Cl.
*G01N 33/86* (2006.01)
*G01N 33/80* (2006.01)

(56) References Cited

U.S. PATENT DOCUMENTS

| | | |
|---|---|---|
| 2015/0323480 A1 | 11/2015 | Brun et al. |
| 2015/0346125 A1 | 12/2015 | Hayashi et al. |

FOREIGN PATENT DOCUMENTS

| | | | |
|---|---|---|---|
| CN | 104937400 A | 9/2015 | |
| EP | 1950567 A1 | 7/2008 | |
| EP | 2947451 A1 | 11/2015 | |
| EP | 2950087 A1 | 12/2015 | |
| JP | 2010-181400 A | 8/2010 | |
| KR | 10-2008-0077355 A | 8/2008 | |
| KR | 10-2015-0108818 A | 9/2015 | |
| WO | 2007/046450 A1 | 4/2007 | |
| WO | WO-2013153735 A1 * | 10/2013 | ........... G01N 27/026 |
| WO | 2014/112227 A1 | 7/2014 | |
| WO | 2014/115478 A1 | 7/2014 | |
| WO | 2015/119115 A1 | 8/2015 | |

OTHER PUBLICATIONS

Wolf, M. et al. "Broadband dielectric spectroscopy on human blood." Biochimica et Biophysica Acta (2011) 1810 727-740. (Year: 2011).*

International Search Report and Written Opinion of PCT Application No. PCT/JP2016/056020, dated Apr. 5, 2016, 10 pages of ISRWO.

* cited by examiner

ELECTRICAL MEASUREMENT METHOD, ELECTRICAL MEASUREMENT DEVICE, AND BLOOD CONDITION ANALYSIS SYSTEM

CROSS REFERENCE TO RELATED APPLICATIONS

This application is a U.S. National Phase of International Patent Application No. PCT/JP2016/056020 filed on Feb. 29, 2016, which claims priority benefit of Japanese Patent Application No. JP 2015-072656 filed in the Japan Patent Office on Mar. 31, 2015. Each of the above-referenced applications is hereby incorporated herein by reference in its entirety.

TECHNICAL FIELD

The present technology relates to an electrical measurement method. More specifically, the present technology relates to a method, an electrical measurement device, and a blood condition analysis system for measuring an electrical characteristic of a blood sample including at least a blood cell component and a plasma component.

BACKGROUND ART

Methods for clinical analysis of the condition of blood include, for example, blood coagulation tests. General known blood coagulation tests include blood coagulation tests represented by prothrombin time (PT) and activated partial thromboplastin time (APTT). These methods include analyzing proteins involved in coagulation reaction and contained in plasma obtained by centrifuging a blood sample. In this field, such methods are technically established, and needs in medical practice have been considered to be nearly satisfied.

However, the above methods are not enough to meet the need for accurate and convenient examination of comprehensive coagulation status of patients, for example, in perioperative (acute phase) therapy where rapidity is required. Specifically, not only surgical bleeding but also coagulation abnormalities-induced bleeding may continue in major surgery such as cardiac surgery accompanied by extracorporeal circulation using a heart-lung machine, severe external injury therapy, or liver transplantation surgery. Nonetheless, the results of conventional coagulation tests are often inconsistent with actual clinical conditions because in the tests, cell components such as platelets and erythrocytes, which play an important role in coagulation reactions in vivo, are removed by centrifugation.

In addition, the coagulation status of patients can greatly fluctuate during the perioperative stage, in which bleeding tendency can often turn into thrombotic tendency. However, PT and APTT tests are for bleeding tendency, and highly sensitive test methods for thrombotic tendency have not been established yet.

For acute-phase comprehensive coagulation tests, thromboelastometry, in which changes in viscoelasticity associated with the blood coagulation process are dynamically measured, has been commercialized under the names TEG (registered trademark) and ROTEM (registered trademark) by Western companies. However, sufficiently widespread use of these methods may be hindered, for example, for the following major reasons: (1) the measurement is not automated and the test results depend on the operator's manual procedure; (2) the measurement is vulnerable to vibrations; (3) the quality control (QC) procedure is complicated and the QC reagents are expensive; and (4) the interpretation of the output signals (thromboelastogram) requires a lot of skill. At present, therefore, blood products are still often prophylactically or empirically administered to patients who would otherwise not need to receive blood transfusion if comprehensive coagulation tests are performed, which not only increases the risk of, for example, infectious diseases but also causes a waste of blood products and an increase in medical costs.

Now, techniques for simply and accurately evaluating the degree of blood coagulation are being developed. For example, Patent Document 1 discloses a technique for obtaining information on blood coagulation from the permittivity of blood, and describes a blood coagulation system analysis device including: a pair of electrodes; means for applying an alternating voltage to the pair of electrodes at predetermined time intervals; means for measuring the permittivity of blood disposed between the pair of electrodes; and means for analyzing the level of activity of the blood coagulation system using the permittivity of blood measured at the predetermined time intervals after the action of an anticoagulant on the blood is stopped.

CITATION LIST

Patent Documents

Patent Document 1: Japanese Patent Application Laid-Open No. 2010-181400

SUMMARY OF THE INVENTION

Problems to be Solved by the Invention

In a case where various measurements or evaluations are performed using blood samples containing a blood cell component and a plasma component, sedimentation of blood cells (hereinafter also referred to as "blood sedimentation") occurs with time. In some cases, blood sedimentation occurs as mentioned above, before the phenomenon to be measured, such as coagulation reaction, so that accurate measurement can not be performed.

It is therefore a main object of the present technology to provide a technique that allows high-accuracy electrical measurement without the influence of blood sedimentation in a case where various measurements or evaluations are performed using blood samples containing a blood cell component and a plasma component.

Solutions to Problems

Specifically, the present technology first provides an electrical measurement method for electrically measuring a blood sample including at least a blood cell component and a plasma component, the electrical measurement method including the step of adding a blood sedimentation inhibitor to the blood sample.

The blood sedimentation inhibitor for use in the electrical measurement method according to the present technology may inhibit blood sedimentation in any specific way possible. For example, the blood sedimentation inhibitor may inhibit blood sedimentation by increasing the specific gravity and/or viscosity of the plasma component.

The blood sedimentation inhibitor may be a non-cationic water-soluble compound.

In this case, the water-soluble compound may be, for example, a non-cationic carbohydrate, a polyhydric alcohol, or a polyamino acid. More specifically, the blood sedimentation inhibitor may be one or more compounds selected from the group consisting of dextran, sucrose, polyethylene glycol, carboxymethyl dextran, and collagen peptide.

The electrical measurement method according to the present technology may further include an addition amount control step including controlling the amount of addition of the blood sedimentation inhibitor on the basis of an electrical characteristic of the blood sample.

In addition, the electrical measurement method may further include a blood condition analysis step including analyzing the condition of blood on the basis of an electrical characteristic of the blood sample.

In this case, the extent of delay in blood sedimentation or the degree of blood coagulation may be analyzed in the blood condition analysis step.

The present technology also provides an electrical measurement device for electrically measuring a blood sample including at least a blood cell component and a plasma component, the electrical measurement device including an addition unit configured to add a blood sedimentation inhibitor to the blood sample.

The electrical measurement device according to the present technology may further include a blood condition analysis unit configured to analyze the condition of blood on the basis of an electrical characteristic of the blood sample.

In this case, the blood condition analysis unit may be configured to analyze the extent of delay in blood sedimentation or the degree of blood coagulation.

The present technology further provides a blood condition analysis system for analyzing the condition of a blood sample including at least a blood cell component and a plasma component, the blood condition analysis system including: an electrical measurement device having an addition unit configured to add a blood sedimentation inhibitor to the blood sample; and a blood condition analysis device including a blood condition analysis unit configured to analyze the condition of blood on the basis of an electrical characteristic of the blood sample.

The blood condition analysis system according to the present technology may further include a server configured to store the results of measurement by the electrical measurement device and/or the results of analysis by the blood condition analysis device.

In this case, the server may be connected to the electrical measurement device and/or the blood condition analysis device via a network.

In addition, the present technology also provides a blood sedimentation inhibitor for use in electrical measurement of a blood sample including at least a blood cell component and a plasma component, the blood sedimentation inhibitor including a non-cationic water-soluble compound and being capable of increasing the specific gravity and/or the viscosity of the plasma component.

The blood sedimentation inhibitor according to the present technology is a material having no adverse effect on blood condition analysis based on an electrical characteristic of the blood sample.

Effects of the Invention

The present technology allows high-accuracy electrical measurement without the influence of blood sedimentation in a case where various measurements, evaluations, or analyses are performed using blood samples containing a blood cell component and a plasma component.

It will be understood that the effects described herein are non-limiting and the present technology may bring about any of the effects described herein.

MODE FOR CARRYING OUT THE INVENTION

Hereinafter, preferred embodiments for carrying out the present technology will be described with reference to the drawings. It will be understood that the embodiments described below are typical embodiments of the present technology and should not be construed as limiting the scope of the present technology. Furthermore, descriptions will be provided in the following order.

Figure 1:
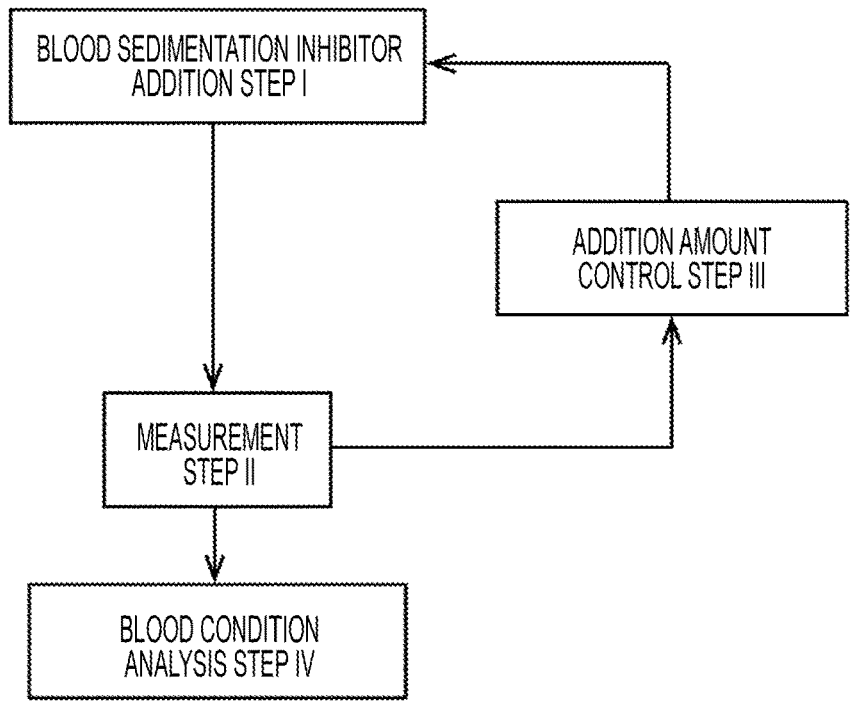
FIG. 1 is a process chart of an electrical measurement method according to the present technology.

1. Electrical measurement method
(1) Blood sedimentation inhibitor addition step I and blood sedimentation inhibitor
(2) Measurement step II
(3) Addition amount control step III
(4) Blood condition analysis step IV
(5) Blood sample
2. Electrical measurement device 1
(1) Blood sedimentation inhibitor addition unit 11
(2) Measurement unit 12
(3) Addition amount control unit 13
(4) Blood condition analysis unit 14
(5) Storage unit 15
3. Blood condition analysis system 10
(1) Electrical measurement device 1
(2) Blood condition analysis device 101
(3) Server 102
(4) Display unit 103
(5) User interface 104
1. Electrical Measurement Method FIG. 1 is a process chart of an electrical measurement method according to the present technology. The electrical measurement method according to the present technology is a method for electrically measuring a blood sample including at least a blood cell component and a plasma component (hereinafter, such a blood sample is also referred to simply as a "blood sample"), and includes at least a blood sedimentation inhibitor addition step I and a measurement step II. In addition, if necessary, for example, an addition amount control step III and a blood condition analysis step IV may also be performed. Hereinafter, each step will be described in detail.

(1) Blood Sedimentation Inhibitor Addition Step I and Blood Sedimentation Inhibitor The blood sedimentation inhibitor addition step I is the step of adding a blood sedimentation inhibitor to a blood sample including at least a blood cell component and a plasma component.

Blood sedimentation occurs with time during various measurements or evaluations using blood samples containing a blood cell component and a plasma component. In conventional technologies, therefore, blood sedimentation-induced measurement anomalies or errors or other problems are prevented by, for example, issuing a warning upon detection of blood sedimentation anomaly, introducing a system for stopping measurements, or applying mechanical action such as stirring. In some cases, however, the system for issuing a warning or stopping measurements can make impossible the measurement of samples in which blood sedimentation occurs extraordinarily quickly. In addition, the method of applying mechanical action to suppress blood sedimentation can mechanically stimulate samples, for example, which can activate blood platelets or other components to affect changes in blood condition, such as blood coagulation reaction.

Therefore, the inventors have conducted extensive studies on techniques for preventing blood sedimentation-induced measurement anomalies or errors and other problems. As a result, the inventors have found that there are many materials having a low impact on changes in blood condition and being capable of preventing blood sedimentation even though in the case of evaluation and analysis of the condition of blood, technical common knowledge is that the addition of drugs and other materials should be kept minimal in order to minimize the influence on changes in blood condition. Thus, the inventors have achieved high-accuracy electrical measurement by performing the step of adding a blood sedimentation inhibitor to blood samples before measurement.

The blood sedimentation inhibitor for use in the electrical measurement method according to the present technology may be one or more freely selected from any known materials that are capable of inhibiting blood sedimentation and do not impair the effect of the present technology. Specifically, not to impair the effect of the present technology may be, for example, not to have any effect on the electrical characteristic parameter used for analyzing the condition of blood on the basis of the results obtained by electrical measurement. In other words, even if the electrical measurement value changes, it will be enough that there is no influence on the parameter extracted for the analysis. Specifically, for example, the time at which an electrical characteristic increases sharply may be used as a parameter for the analysis. In this case, no change in the time of the increase will mean no influence on the analysis even if the rate of increase in the electrical characteristic changes.

The method of inhibiting blood sedimentation using the blood sedimentation inhibitor in the present technology may be, for example, to increase the specific gravity and/or viscosity of the plasma component so that sedimentation of the blood cell component can be inhibited.

More specifically, for example, the blood sedimentation inhibitor may be a non-cationic water-soluble compound. More specifically, the blood sedimentation inhibitor may be, for example, one or more selected from the group consisting of carbohydrates such as dextran, carboxymethyl dextran, and sucrose; polyhydric alcohols such as polyethylene glycol; and polyamino acids such as collagen peptides. It should be noted that the effect of these compounds may vary with molecular weight. For example, the molecular weight of dextran is preferably from 1,000 to 100,000, more preferably from 20,000 to 40,000. Further, for example, the molecular weight of polyethylene glycol is preferably from 200 to 100,000, more preferably from 5,000 to 7,000.

Any one or more known addition methods that do not impair the effect of the present technology may be freely used for adding the blood sedimentation inhibitor. Examples of such methods include a method of injecting the blood sedimentation inhibitor to a container containing a blood sample and a method of adding a blood sample to a container containing the blood sedimentation inhibitor.

(2) Measurement Step II

The measurement step II is the step of measuring an electrical characteristic of the blood sample. Examples of electrical characteristics that can be measured in the electrical measurement method according to the present technology include permittivity, impedance, admittance, capacitance, conductance, conductivity, and phase angle. These electrical characteristics can be converted to one another by the mathematical formulas shown in Table 1 below. Therefore, for example, the evaluation result obtained by evaluating the hematocrit value and/or the hemoglobin amount using the result of permittivity measurement of a blood sample will be the same as the evaluation result obtained using the result of impedance measurement of the same blood sample. Many of these electrical quantities and physical property values can be expressed using complex numbers, which will simplify the conversion formulas.

TABLE 1

<Major interchangeable electrical quantities and physical property values>

| Electrical quantities and physical property values | Symbol | Complex number expression |
|---|---|---|
| Voltage | V | $V^* = \|V\|\exp j(\omega t + \phi)$ |
| Current | I | $I^* = \|I\|\exp j(\omega t + \varphi)$ |
| Impedance | Z | $Z^* = R + jX$ (R: Resistance, X: Reactance) |
| Admittance | Y | $Y^* = G + jB$ (G: Conductance, B: Susceptance) |
| Capacitance | C | $C^* = C - jG/\omega$ |
| Conductance | G | $G^* = G + j\omega C$ |
| Loss tangent (Dielectric loss tangent) | D or tanδ | |
| Loss angle | δ | |
| Phase angle | θ | |
| Q value | Q | |
| Permittivity | ε | $\varepsilon^* = \varepsilon - j\kappa/\omega\varepsilon_0$ |
| Conductivity | κ | $\kappa^* = \kappa + j\omega\varepsilon_{0e}$ |

<Mathematical formulas associating respective electrical quantities and physical property values>

$Z^* = V^*/I^*$
$\theta = \phi - \varphi$
$Y^* = 1/Z^*$
$C = B/\omega$
$D = \tan\delta = G/\omega C = 1/Q$
$\varepsilon^* = C^*/C_0$
$\kappa^* = j\omega\varepsilon_0\varepsilon^*$ ω: Angular frequency
$\varepsilon_0$: Vacuum permittivity (constant)
$C_0$: Constant depending on measurement device or other factors
Values with
*Complex numbers In the measurement step II, the frequency band for the electrical measurement can be appropriately selected according to the condition of the blood sample to be measured, the purpose of the measurement, or other factors. For example, in a case where the electrical characteristic to be measured is impedance, changes can be observed in the frequency bands shown in Table 2 below according to changes in blood condition.

TABLE 2

| | Impedance | |
| --- | --- | --- |
| Change in blood condition | Frequency at which change is observable | Frequency at which change is more significant |
| Blood coagulation (blood clotting) | 1 kHz to 50 MHz | 3 MHz to 15 MHz |
| Fibrin formation | 1 kHz to 50 MHz | 3 MHz to 15 MHz |
| Fibrin clot formation | 1 kHz to 50 MHz | 3 MHz to 15 MHz |
| Blood clot formation | 1 kHz to 50 MHz | 3 MHz to 15 MHz |
| Erythrocyte rouleaux formation | 500 kHz to 25 MHz | 2 MHz to 10 MHz |
| Blood agglutination | 1 kHz to 50 MHz | 500 kHz to 5 MHz |
| Erythrocyte sedimentation (blood sedimentation) | 1 kHz to 50 MHz | 100 kHz to 40 MHz |
| Clot retraction | 1 kHz to 50 MHz | 10 kHz to 100 kHz |
| Hemolysis | 1 kHz to 50 MHz | 3 MHz to 15 MHz |
| Fibrinolysis | 1 kHz to 50 MHz | 3 MHz to 15 MHz |

For example, for the purpose of predicting or detecting blood coagulation (blood clotting), the impedance is preferably measured at a frequency of 1 kHz to 50 MHz, more preferably at a frequency of 3 MHz to 15 MHz. Thus, a parameter may be selected in advance according to the blood sample condition or the measurement purpose so that the preferred frequency band can be automatically selected as shown in Table 2 above.

(3) Addition Amount Control Step III

The addition amount control step III is the step of controlling the amount of addition of the blood sedimentation inhibitor on the basis of the electrical characteristic of the blood sample. The addition amount control step III is not indispensable in the present technology. However, performing the addition amount control step III allows measurement with higher accuracy.

Specifically, for example, the addition amount control step III may be performed by a method that includes calculating the blood sedimentation rate on the basis of the electrical characteristic measured in advance and controlling the amount of addition of the blood sedimentation control agent in accordance with the blood sedimentation rate. Alternatively, for example, in a case where the electrical characteristic measured in the measurement step II shows an abnormal value and suggests blood sedimentation anomalies, the addition amount control step III may be performed by a method that includes stopping the measurement, calculating the blood sedimentation rate on the basis of the measured electrical characteristic, controlling the amount of addition of the blood sedimentation control agent in accordance with the blood sedimentation rate, and restarting the measurement.

(4) Blood Condition Analysis Step IV

In the blood condition analysis step IV, the condition of blood is analyzed on the basis of the electrical characteristic of the blood sample. The blood condition analysis step IV is not indispensable in the electrical measurement method according to the present technology. Alternatively, for example, another analysis method may be used to analyze the condition of the blood sample on the basis of the measurement result obtained by the electrical measurement method according to the present technology.

The blood condition that can be analyzed in the blood condition analysis step IV of the electrical measurement method according to the present technology may be any phenomenon in which changes in the electrical characteristic of blood can be observed as a result of changes in blood condition. In addition, changes in various conditions may be analyzed and evaluated. Examples of such a phenomenon include blood coagulation (blood clotting), fibrin formation, fibrin clot formation, clot formation, platelet aggregation, erythrocyte rouleaux formation, blood agglutination, erythrocyte sedimentation (blood sedimentation), clot retraction, hemolysis such as fibrinogenolysis, and fibrinolysis.

(5) Blood Sample

In the electrical measurement method according to the present technology, any blood sample containing at least a blood cell component and a plasma component may be freely selected as the object to be measured. Specific examples of the blood sample include whole blood or a dilution thereof, and blood samples containing any of various reagents or drugs such as anticoagulation stopping agents, coagulation activators, anticoagulants, platelet activators, and antiplatelet agents.

2. Electrical Measurement Device 1

Figure 2:
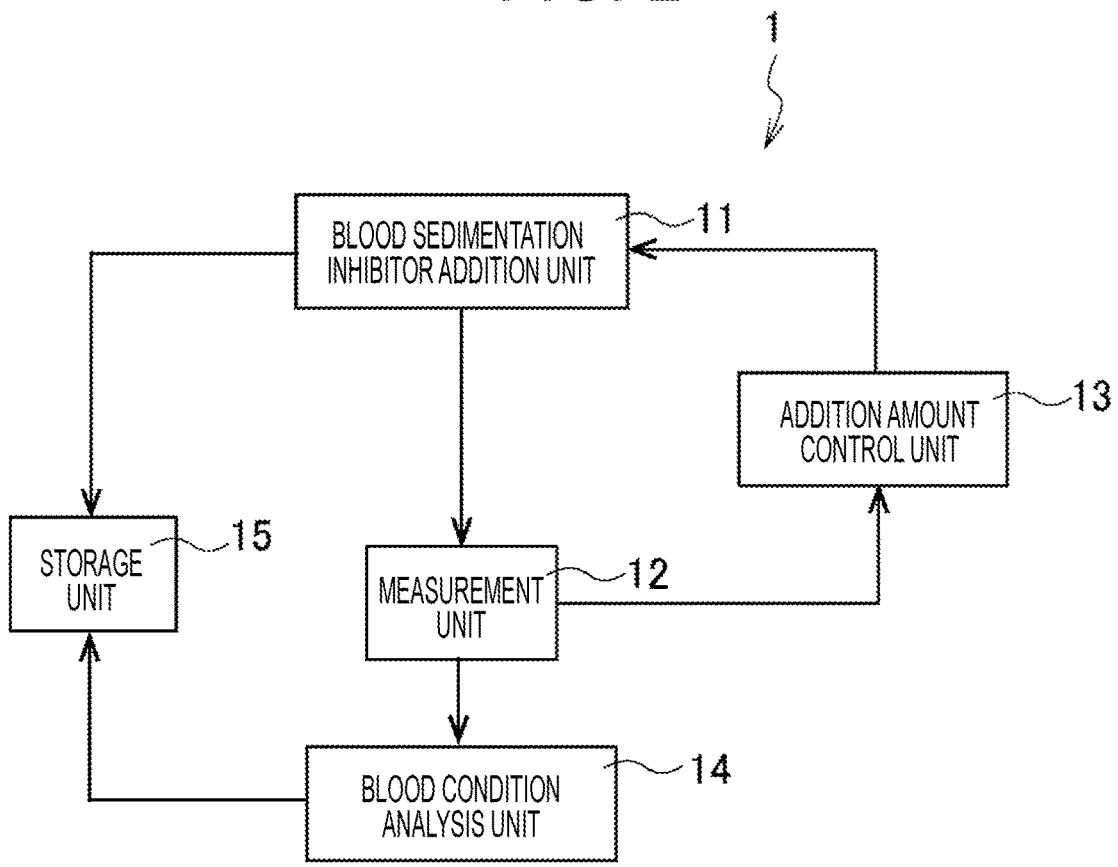
FIG. 2 is a schematic conceptual diagram schematically showing the concept of an electrical measurement device 1 according to the present technology.

FIG. 2 is a schematic conceptual diagram schematically showing the concept of an electrical measurement device 1 according to the present technology. The electrical measurement device 1 according to the present technology includes at least a blood sedimentation inhibitor addition unit 11 and a measurement unit 12. In addition, if necessary, the device 1 may include, for example, an addition amount control unit 13, a blood condition analysis unit 14, and a storage unit 15. Hereinafter, each unit will be described in detail.

(1) Blood Sedimentation Inhibitor Addition Unit 11

The blood sedimentation inhibitor addition unit 11 is configured to add a blood sedimentation inhibitor to a blood sample containing at least a blood cell component and a plasma component. The details of the method of adding the blood sedimentation inhibitor by the blood sedimentation inhibitor addition unit 11 and the details of the blood sedimentation inhibitor type and other conditions are the same as those in the blood sedimentation inhibitor addition step I of the electrical measurement method described above.

(2) Measurement Unit 12

The measurement unit 12 is configured to measure an electrical characteristic of the blood sample. The electrical characteristic measurable by the electrical measurement device 1 according to the present technology and the frequency band are the same as those in the measurement step II of the electrical measurement method described above.

The measurement unit 12 may include one or more blood sample holders. The blood sample holder is not indispensable in the electrical measurement device 1. Alternatively, the measurement unit 12 may also be so designed that, for example, a known cartridge type measurement container can be attached to it.

In a case where the measurement unit 12 has a blood sample holder, the blood sample holder may be designed in any desired form capable of holding, in the measurement unit 12, the blood sample to be measured. For example, one or more cells may be provided on a substrate to function as the blood sample holders, or one or more containers may be provided to function as the sample holders.

In a case where one or more containers are used as the blood sample holders, the containers may be in any form capable of holding the blood sample to be measured, such as a cylindrical form, a polygonal tube form with a polygonal cross-section (a triangular, quadrangular, or polygonal cross-section), a conical form, a polygonal pyramid form with a polygonal cross-section (a triangular, quadrangular, or polygonal cross-section), or a combination of one or more thereof, which may be freely designed according to the condition of the blood sample, the measurement method, or other conditions.

Also, the material used to form the container is not limited, and may be freely selected within a range where there is no influence on the condition of the blood sample to be measured, the measurement purpose, and other conditions. In the present technology, a resin is particularly preferably used to form the container in view of ease of forming or molding and other features. In the present technology, the usable resin may be of any type, and one or more resins suitable for use in holding the blood sample may be freely selected and used. Examples of such resins include hydrophobic and insulating polymers or copolymers, such as polypropylene, polymethyl methacrylate, polystyrene, acrylic, polysulfone, and polytetrafluoroethylene, and polymer blends. Among them, one or more resins selected from polypropylene, polystyrene, acrylic, and polysulfone are particularly preferably used to form the blood sample holder in the present technology. This is because these resins have the property of being less likely to cause blood clots.

The blood sample holder is preferably so designed that it can be air-tightly closed while holding the blood sample. However, the blood sample holder does not needs to be in an air-tight form if the blood sample can be kept stable with no influence on the measurement during the time period required for the measurement of the electrical characteristic of the blood sample.

Any specific method may be selected depending on the form of the blood sample holder and used to introduce the blood sample into the blood sample holder and to air-tightly close the holder. Examples of such a method include a method including providing a lid for the blood sample holder, introducing the blood sample into the blood sample holder with a pipette or other means, and then closing the lid to air-tightly close the blood sample holder; and a method including inserting an injection needle into the blood sample holder through its outer surface, injecting the blood sample into the blood sample holder, and then sealing, with grease or other materials, the portion through which the needle has passed.

The measurement unit 12 may include one or more energization sections. The energization section is not indispensable in the electrical measurement device 1. Alternatively, for example, the blood sample holder may be so designed that electrodes can be inserted into the blood sample holder from the outside so that an external energization device can be used.

The energization section is configured to apply a predetermined voltage to the blood sample at respective preset measurement intervals from the start time at which the energization section receives an instruction to start the measurement or at which the electrical measurement device 1 is turned on.

The electrodes used as parts of the energization section may be formed in any number and made of any material as long as the effect of the present technology is not impaired. The electrodes may include, for example, titanium, aluminum, stainless steel, platinum, gold, copper, graphite, or other materials. In the present technology, an electrically conductive material containing titanium is preferably used to form the electrodes. This is because titanium has the property of being less likely to cause blood clots.

The measurement unit 12 may also be configured to perform a plurality of measurements. The method of performing a plurality of measurements may be, for example, a method of simultaneously performing a plurality of measurements with a plurality of measurement units 12 provided therefor, a method of performing a plurality of measurements by scanning with one measurement unit 12, a method of moving the blood sample holder to perform a plurality of measurements, or a method of selecting, by switching, one or more measurement units 12 for the actual measurement from a plurality of measurement units 12.

The measurement unit 12 preferably has a temperature control function. As shown in the examples below, blood samples can significantly vary in electrical characteristic such as permittivity as the temperature changes. Therefore, the temperature control function provided to the measurement unit 12 can prevent temperature change-induced measurement errors.

(3) Addition Amount Control Unit 13

The addition amount control unit 13 is configured to control the amount of addition of the blood sedimentation inhibitor on the basis of the electrical characteristic of the blood sample. The addition amount control unit 13 is not indispensable in the present technology. However, if provided, the addition amount control unit 13 will make it possible to perform higher-accuracy measurement.

The specific control method performed by the addition amount control unit 13 and other conditions are the same as those in the addition amount control step III of the electrical measurement method described above.

(4) Blood Condition Analysis Unit 14

The blood condition analysis unit 14 is configured to analyze the condition of blood on the basis of the electrical characteristic of the blood sample. The blood condition analysis unit 14 is not indispensable in the electrical measurement device 1 according to the present technology. Alternatively, an external analyzer or other devices may be used to analyze the condition of the blood sample on the basis of the measurement results obtained by the electrical measurement device 1 according to the present technology.

The blood condition that can be analyzed by the blood condition analysis unit 14 of the electrical measurement device 1 according to the present technology is the same as in the blood condition analysis step IV of the electrical measurement method described above.

(5) Storage Unit 15

The electrical measurement device 1 according to the present technology may include a storage unit 15 configured to store data on the amount of the blood sedimentation inhibitor added by the blood sedimentation inhibitor addition unit 11, the results of each analysis performed by the blood condition analysis unit 14, the results of the measurement performed by the measurement unit 12, and other information. The storage unit 15 is not indispensable in the electrical measurement device 1 according to the present technology. Alternatively, an external storage device may be connected to the device 1 to store each result.

In the electrical measurement device 1 according to the present technology, the storage unit 15 may be provided separately for each unit, or the electrical measurement device 1 may be so designed that various results obtained by the respective units are stored in one storage unit 15.

3. Blood Condition Analysis System 10

Figure 3:
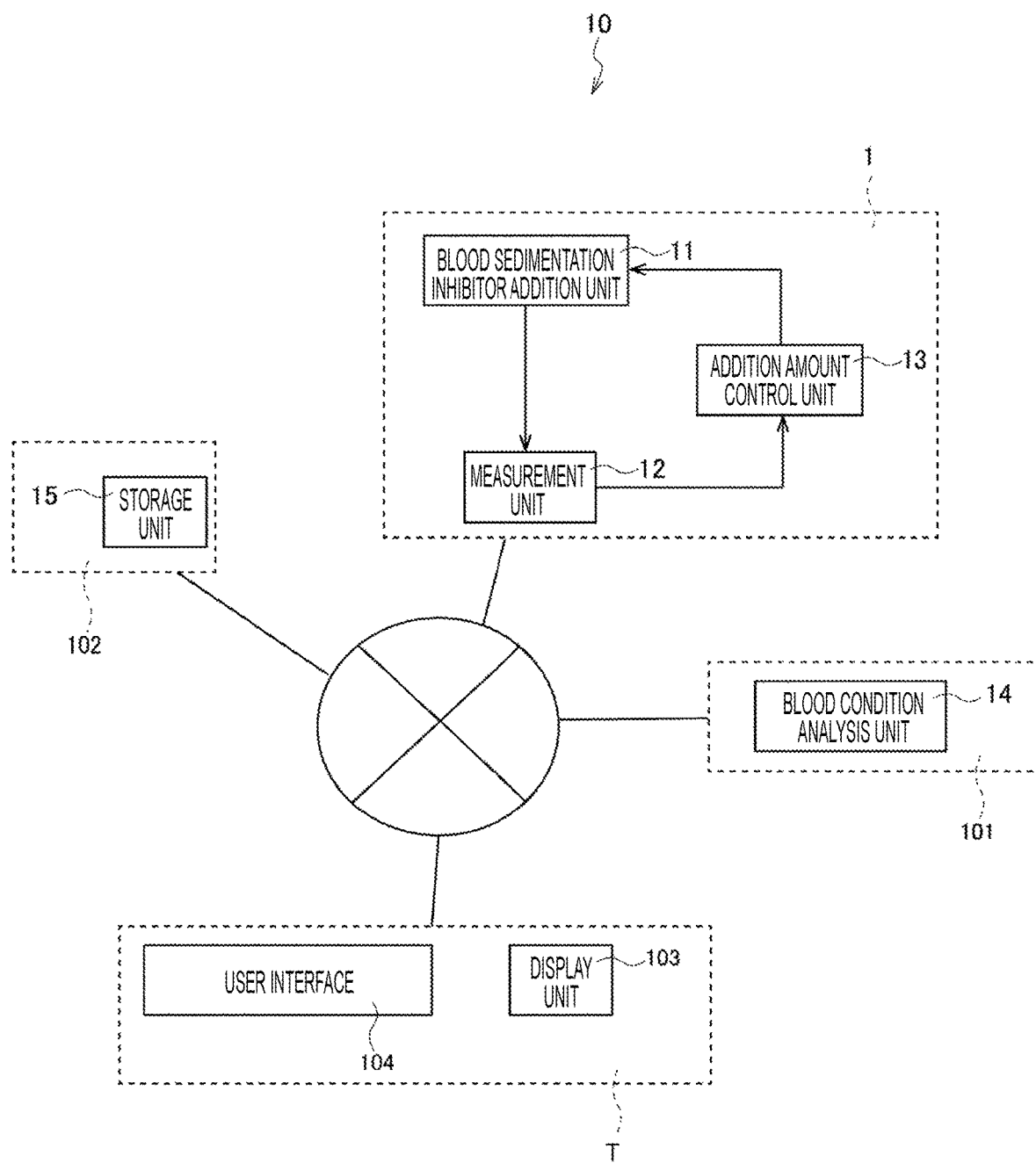
FIG. 3 is a schematic conceptual diagram schematically showing the concept of a blood condition analysis system 10 according to the present technology.

FIG. 3 is a schematic conceptual diagram schematically showing the concept of a blood condition analysis system 10 according to the present technology. The blood condition analysis system 10 according to the present technology includes at least an electrical measurement device 1 and a blood condition analysis device 101, which are major components. In addition, if necessary, the system 10 may also include, for example, a server 102, a display unit 103, and a user interface 104. Hereinafter, each component will be described in detail.

(1) Electrical Measurement Device 1

The electrical measurement device 1 includes at least the blood sedimentation inhibitor addition unit 11 and the measurement unit 12. In addition, if necessary, the electrical measurement device 1 may include the addition amount control unit 13 and other components. In this regard, each component of the electrical measurement device 1 is the same as that of the electrical measurement device 1 described above, and, therefore, the description thereof is omitted here.

(2) Blood Condition Analysis Device 101

The blood condition analysis device 101 includes a blood condition analysis unit 14 configured to analyze the condition of blood on the basis of the electrical characteristic of the blood sample. In this regard, the blood condition analysis unit 14 is the same as the blood condition analysis unit 14 of the electrical measurement device 1 described above, and, therefore, the description thereof is omitted here.

(3) Server 102

The server 102 includes a storage unit 15 configured to store the results of the measurement by the electrical measurement device 1 and/or the results of the analysis by the blood condition analysis device 101. The details of the storage unit 15 are the same as those of the storage unit 15 in the electrical measurement device 1 described above.

(4) Display Unit 103

The display unit 103 is configured to display, for example, the results of the measurement by the electrical measurement device 1 and/or the results of the analysis by the blood condition analysis device 101. A plurality of display units 103 may be provided for the respective data or results to be displayed, or one display unit 103 may be provided to display all data or results. The display unit 103 may be provided as a terminal device T together with the user interface 104 described below and other components.

(5) User Interface 104

The user interface 104 is a section provided for user operation. The user can access each component of the blood condition analysis system 10 according to the present technology through the user interface 104.

In the blood condition analysis system 10 according to the present technology described above, the electrical measurement device 1, the blood condition analysis device 101, the server 102, the display unit 103, and the user interface 104 may be connected to one another via a network.

EXAMPLES

Hereinafter, the present invention will be described in more detail with reference to examples. It will be understood that the examples described below are mere typical examples of the present invention and should not be construed as limiting the scope of the present invention.

Experimental Example 1

Experimental Example 1 was performed to determine whether and how the results of measurement of an electrical characteristic differ between a case where a compound with an inhibitory effect on blood sedimentation is used in the measurement of the electrical characteristic of blood samples and a case where a compound with no inhibitory effect on blood sedimentation is used in the measurement. In this experiment, permittivity was used as an example of the electrical characteristic. In addition, the samples used were whole blood from healthy subjects. Furthermore, citric acid was added as an anticoagulant to the blood samples, and the resulting samples were subjected to measurement without addition of a coagulation stopping agent to the samples in order to examine only the inhibitory effect on blood sedimentation.

[Adjustment of Blood Sample with Sedimentation Abnormalities]

Blood from healthy subjects was centrifuged at 500 G for 5 minutes, so that the plasma component was collected. A blood sample with sedimentation abnormalities was prepared by adding 0.8 mL of the collected plasma component to 2 mL of the healthy subject blood.

Example 1

Polyethylene glycol 6000 as an example of the blood sedimentation inhibitor was dissolved at a concentration of 10% w/v in PBS. The blood sedimentation inhibitor-containing PBS solution was added in an amount of 10% to the blood sample with sedimentation abnormalities, prepared as described above, so that a sample of Example 2 was obtained.

Example 2

A sample of Example 2 was prepared by a method similar to that in Example 1, except that a collagen peptide was used as an example of the blood sedimentation inhibitor.

Comparative Example 1

A sample of Comparative Example 1 was prepared by a method similar to that in Example 1, except that polyvinylpyrrolidone (K-90) was used as an example of a compound with no inhibitory effect on blood sedimentation.

Comparative Example 2

A sample of Comparative Example 2 was prepared by a method similar to that in Example 1, except that DEAE-dextran, a cationic compound, was used as an example of a compound with no inhibitory effect on blood sedimentation.

[Control]

A control sample was prepared by adding blood sedimentation inhibitor-free PBS in an amount of 10% to the blood sample with sedimentation abnormalities, prepared as described above.

[Measurement of Electrical Characteristic]

The permittivity of 180 μL of each of the samples of Examples 1 and 2, Comparative Examples 1 and 2, and Control prepared as described above was measured at a frequency of 1 MHz over time.

[Results]

Figure 4:
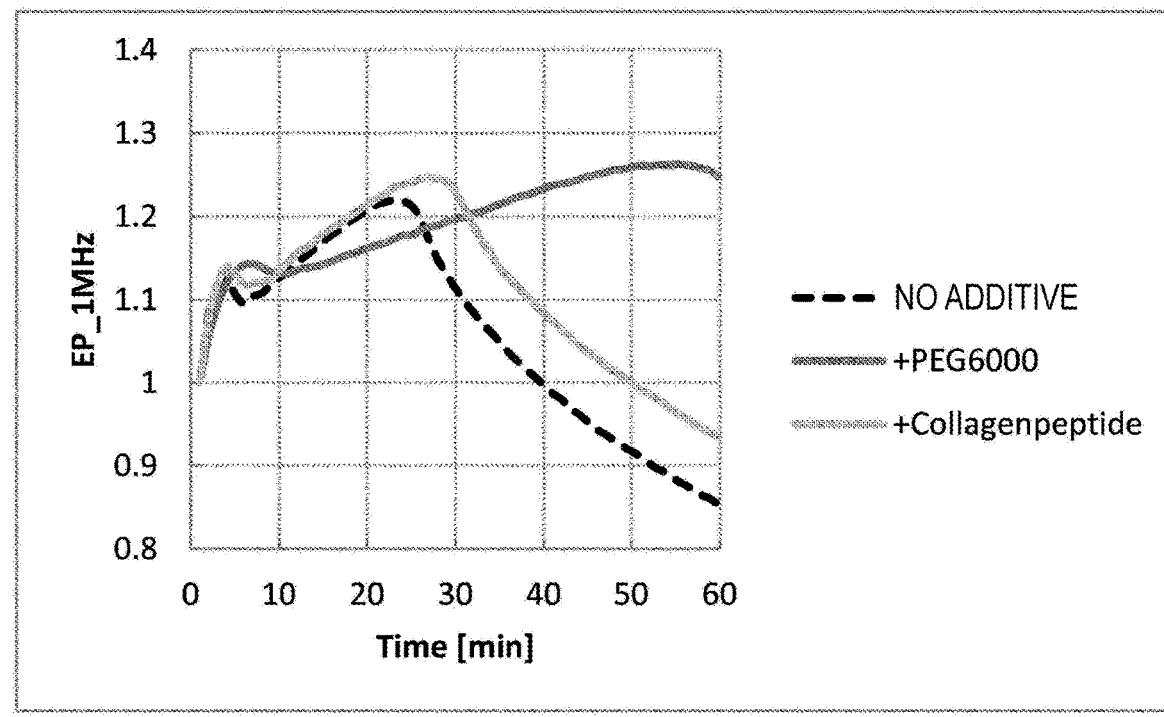
FIG. 4 is a drawing-substitute graph showing the permittivity measurement results of Examples 1 and 2 in Experimental Example 1.
Figure 5:
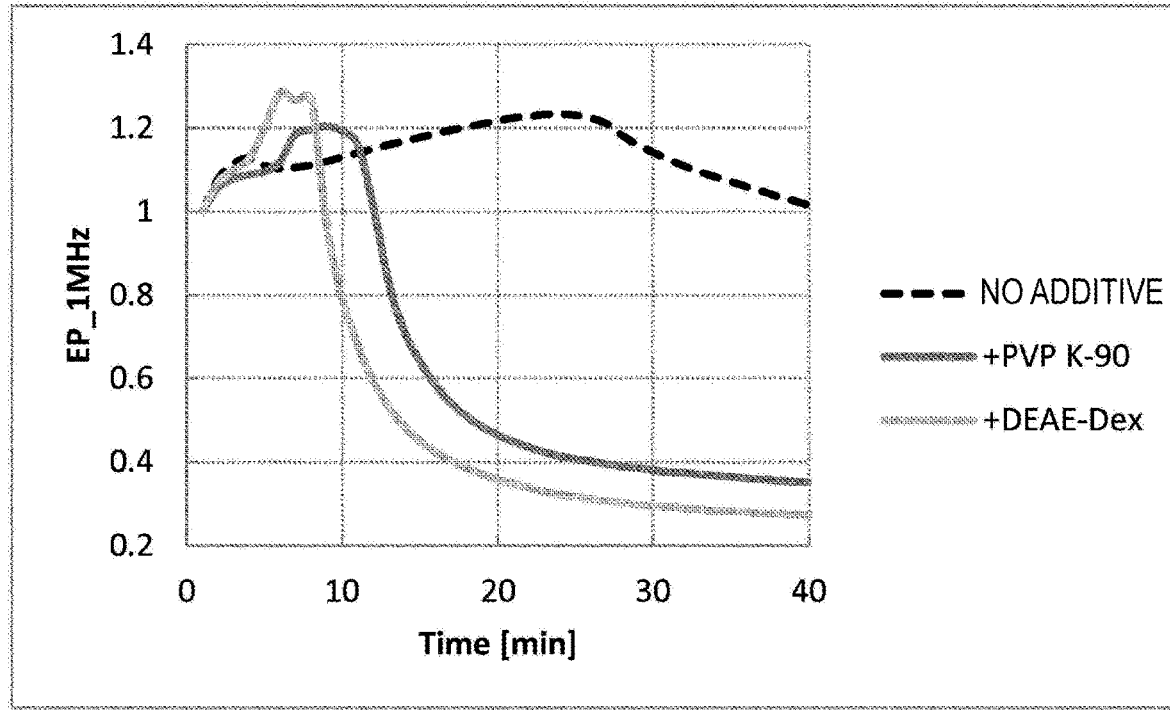
FIG. 5 is a drawing-substitute graph showing the permittivity measurement results of Comparative Examples 1 and 2 in Experimental Example 1.

FIGS. 4 and 5 show the measurement results of Examples 1 and 2 and the measurement results of Comparative Examples 1 and 2, respectively. FIG. 4 shows that the permittivity peak appears later in Examples 1 and 2, where a blood sedimentation inhibitor is added, than in the control. On the other hand, it is apparent that the permittivity peak appears earlier in Comparative Examples 1 and 2, where a compound with no inhibitory effect on blood sedimentation is added, than in the control.

These results have demonstrated that the use of each blood sedimentation inhibitor shows an about 6% inhibitory effect on blood sedimentation as compared with no addition of the blood sedimentation inhibitor.

Experimental Example 2

Experimental Example 2 was performed to determine whether and how the results of measurement of an electrical characteristic differ between a case using a compound having an inhibitory effect on blood sedimentation and having no influence on the electrical characteristic parameter used for analysis and a case using a compound having an influence on the electrical characteristic parameter. In this experimental example, permittivity was used as an example of the electrical characteristic. In addition, a coagulation start-indicating parameter for use in blood coagulation analysis was focused on as an example of the electrical characteristic parameter for use in analysis. Furthermore, in Experimental Example 2, measurement was performed on blood samples containing citric acid added as an anticoagulant with calcium chloride added as a blood coagulation stopping agent.

Example 3

Carboxymethyl dextran as an example of the blood sedimentation inhibitor was dissolved at a concentration of 10% w/v in PBS. The carboxymethyl dextran-containing PBS solution was added in an amount of 10% to a whole blood sample with a high blood sedimentation rate, so that a sample of Example 3 was obtained.

[Control for Example]

A control sample was prepared by adding a blood sedimentation inhibitor-free PBS in an amount of 10% to the same whole blood sample as in Example 3.

Comparative Example 3

Betaine was dissolved at a concentration of 10% w/v in PBS. The resulting blood sedimentation inhibitor-containing PBS solution was added in an amount of 10% to a blood sample with sedimentation abnormalities, prepared by a method similar to that in Experimental Example 1, so that a sample of Comparative Example 3 was obtained.

[Control for Comparative Example]

A control sample was prepared by adding a blood sedimentation inhibitor-free PBS in an amount of 10% to a blood sample with sedimentation abnormalities, prepared by a method similar to that in Experimental Example 1.

[Measurement of Electrical Characteristic]

The permittivity of 180 μL of each of the samples of Example 3, Control for Example, Comparative Example 3, and Control for Comparative Example, prepared as described above, was measured at a frequency of 1 MHz over time.

[Results]

Figure 6:
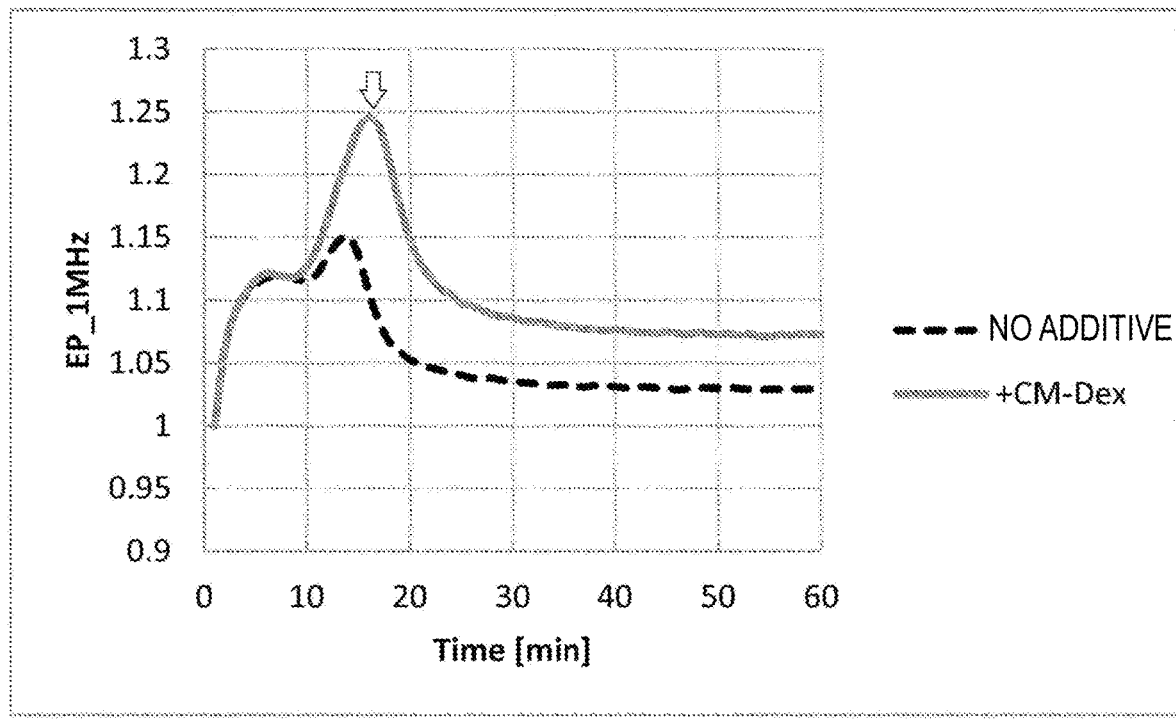
FIG. 6 is a drawing-substitute graph showing the permittivity measurement result of Example 3 in Experimental Example 2.
Figure 7:
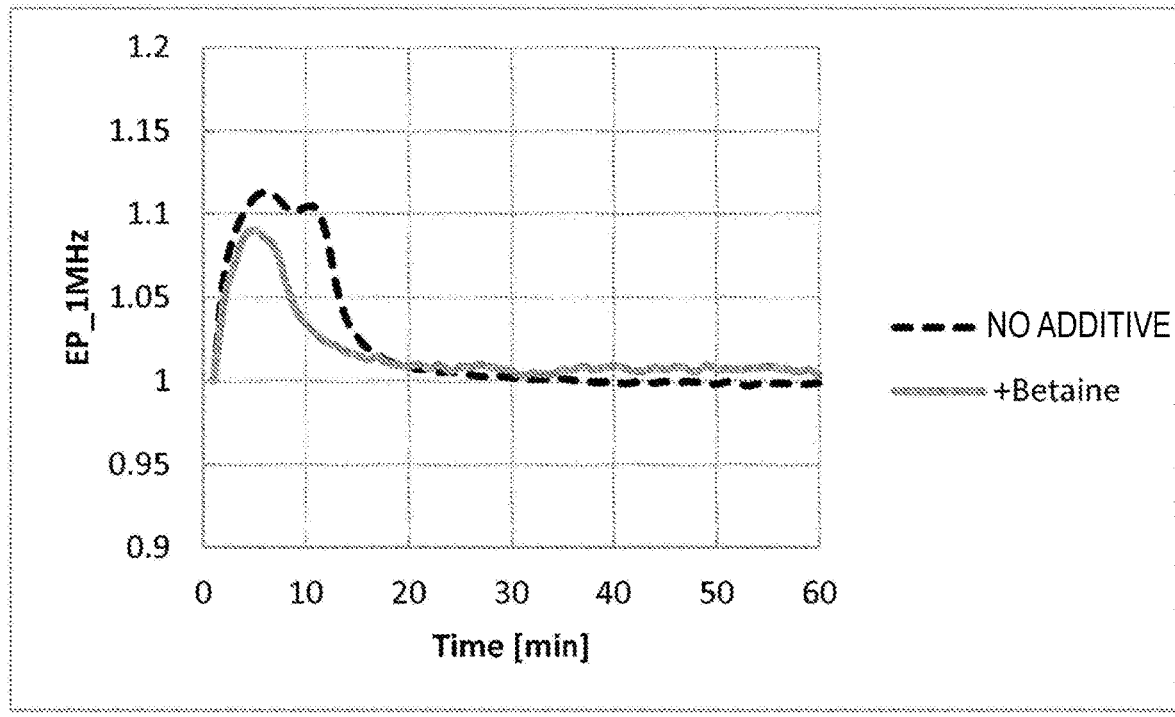
FIG. 7 is a drawing-substitute graph showing the permittivity measurement result of Comparative Example 3 in Experimental Example 2.

FIGS. 6 and 7 show the measurement results of Example 3 and the measurement results of Comparative Example 3, respectively. As shown in FIG. 6, the sample of Example 3 containing carboxymethyl dextran exhibited a signal behavior similar to that of the control sample, and the blood coagulation start time was successfully analyzed using a parameter (see the arrow in FIG. 6) indicating the time at which coagulation started. On the other hand, the sample of Comparative Example 3 containing betaine exhibited a signal behavior completely different from that of the control sample, and it was impossible to extract any parameter indicating the coagulation start time.

These results suggest that both carboxymethyl dextran and betaine have an inhibitory effect on blood sedimentation. However, it has been found that carboxymethyl dextran is usable as the blood sedimentation inhibitor according to the present technology because it has no adverse effect on the analysis whereas betaine is not usable as the blood sedimentation inhibitor according to the present technology because it has an adverse effect on the analysis.

Note that the present technology may also have the following features.

(1)

An electrical measurement method for electrically measuring a blood sample including at least a blood cell component and a plasma component, the electrical measurement method including the step of adding a blood sedimentation inhibitor to the blood sample.

(2)

The electrical measurement method according to item (1), in which the blood sedimentation inhibitor is capable of increasing the specific gravity and/or the viscosity of the plasma component.

(3)

The electrical measurement method according to item (1) or (2), in which the blood sedimentation inhibitor is a non-cationic water-soluble compound.

(4)

The electrical measurement method according to item (3), in which the water-soluble compound is one or more compounds selected from the group consisting of a carbohydrate, a polyhydric alcohol, and a polyamino acid.

(5)

The electrical measurement method according to item (4), in which the water-soluble compound is one or more compounds selected from the group consisting of dextran, sucrose, polyethylene glycol, carboxymethyl dextran, and collagen peptide.

(6)

The electrical measurement method according to anyone of items (1) to (5), further including an addition amount control step including controlling the amount of addition of the blood sedimentation inhibitor on the basis of an electrical characteristic of the blood sample.

(7)

The electrical measurement method according to anyone of items (1) to (6), further including a blood condition analysis step including analyzing the condition of blood on the basis of an electrical characteristic of the blood sample.

(8)

The electrical measurement method according to item (7), in which the blood condition analysis step includes analyzing the extent of delay in blood sedimentation.

(9)

The electrical measurement method according to item (7) or (8), in which the blood condition analysis step includes analyzing the degree of blood coagulation.

(10)

An electrical measurement device for electrically measuring a blood sample including at least a blood cell component and a plasma component, the electrical measurement device including an addition unit configured to add a blood sedimentation inhibitor to the blood sample.

(11)

The electrical measurement device according to item (10), further including a blood condition analysis unit configured to analyze the condition of blood on the basis of an electrical characteristic of the blood sample.

(12)

The electrical measurement device according to item (11), in which the blood condition analysis unit is configured to analyze the extent of delay in blood sedimentation.

(13)

The electrical measurement device according to item (11) or (12), in which the blood condition analysis unit is configured to analyze the degree of blood coagulation.

(14)

A blood condition analysis system for analyzing the condition of a blood sample including at least a blood cell component and a plasma component, the blood condition analysis system including:
an electrical measurement device having an addition unit configured to add a blood sedimentation inhibitor to the blood sample; and
a blood condition analysis device including a blood condition analysis unit configured to analyze the condition of blood on the basis of an electrical characteristic of the blood sample.

(15)

The blood condition analysis system according to item (14), further including a server configured to store the results of measurement by the electrical measurement device and/or the results of analysis by the blood condition analysis device.

(16)

The blood condition analysis system according to item (15), in which the server is connected to the electrical measurement device and/or the blood condition analysis device via a network.

(17)

A blood sedimentation inhibitor for use in electrical measurement of a blood sample including at least a blood cell component and a plasma component, the blood sedimentation inhibitor including a non-cationic water-soluble compound and being capable of increasing the specific gravity and/or the viscosity of the plasma component.

(18)

The blood sedimentation inhibitor according to item (17), which has no adverse effect on blood condition analysis based on an electrical characteristic of the blood sample.

REFERENCE SIGNS LIST

I Blood sedimentation inhibitor addition step
II Measurement step
III Addition amount control step
IV Blood condition analysis step
1 Electrical measurement device
11 Blood sedimentation inhibitor addition unit
12 Measurement unit
13 Addition amount control unit
14 Blood condition analysis unit
15 Storage unit
10 Blood condition analysis system
101 Blood condition analysis device
102 Server
103 Display unit
104 User interface

The invention claimed is:

1. An electrical measurement device, comprising:
a measurement unit including an energization section, wherein
the energization section includes a pair of electrodes, and
the energization section is configured to:
apply a specific voltage to a blood sample via the pair of electrodes, and
measure an electrical characteristic of the blood sample based on the application of the specific voltage to the blood sample, wherein the blood sample comprises at least one of a blood cell component or a plasma component; and
an addition amount control unit configured to:
detect a blood sedimentation induced error based on the measured electrical characteristic of the blood sample;
calculate a blood sedimentation rate of the blood sample based on the measured electrical characteristic of the blood sample and the detected blood sedimentation induced error; and
control an amount of a blood sedimentation inhibitor based on the calculated blood sedimentation rate, wherein
the controlled amount of the blood sedimentation inhibitor is added to the blood sample.

2. The electrical measurement device according to claim 1, further comprising a blood condition analysis unit, wherein
the blood condition analysis unit includes an analyzer, and
the analyzer is configured to analyze a condition of the blood sample based on the measured electrical characteristic of the blood sample.

3. The electrical measurement device according to claim 2, wherein the analyzer is further configured to analyze an extent of delay in a blood sedimentation process.

4. The electrical measurement device according to claim 2, wherein the analyzer is further configured to analyze a degree of blood coagulation.

5. A blood condition analysis system, comprising:
an electrical measurement device that comprises:
a measurement unit including an energization section, wherein
the energization section includes a pair of electrodes, and
the energization section is configured to:
apply a specific voltage to a blood sample via the pair of electrodes, and
measure an electrical characteristic of the blood sample based on the application of the specific voltage to the blood sample,
wherein the blood sample comprises at least one of a blood cell component or a plasma component; and
an addition amount control unit configured to:
detect a blood sedimentation induced error based on the measured electrical characteristic of the blood sample;
calculate a blood sedimentation rate of the blood sample based on the measured electrical characteristic of the blood sample and the detected blood sedimentation induced error; and
control an amount of a blood sedimentation inhibitor based on the calculated blood sedimentation rate, wherein the controlled amount of the blood sedimentation inhibitor is added to the blood sample; and a blood condition analysis device that comprises a blood condition analysis unit, wherein
the blood condition analysis unit includes an analyzer, and
the analyzer is configured to analyze the condition of the blood sample based on the measured electrical characteristic of the blood sample.

6. The blood condition analysis system according to claim 5, further comprising a server configured to store at least one of a result of the measurement by the electrical measurement device or a result of the analysis by the blood condition analysis device.

7. The blood condition analysis system according to claim 6, wherein the server is connected to at least one of the electrical measurement device or the blood condition analysis device via a network.

8. The electrical measurement device according to claim 1, wherein the energization section is further configured to apply the specific voltage to the blood sample at each measurement interval of preset measurement intervals.

9. The electrical measurement device according to claim 1, wherein the electrical characteristic corresponds to at least one of admittance, capacitance, conductance, conductivity, or phase angle.

* * * * *